United States Patent
Manasas et al.

(10) Patent No.: US 6,520,996 B1
(45) Date of Patent: Feb. 18, 2003

(54) ORTHOPEDIC IMPLANT

(75) Inventors: Mark Manasas, Dedham, MA (US); Keith Oslakovic, Cambridge, MA (US); Cornel Sultan, Everett, MA (US); John Hamilton, Foxboro, MA (US); Donald Ingber, Boston, MA (US)

(73) Assignee: DePuy AcroMed, Incorporated, Raynham, MA (US)

( * ) Notice: Subject to any disclaimer, the term of this patent is extended or adjusted under 35 U.S.C. 154(b) by 0 days.

(21) Appl. No.: 09/588,167

(22) Filed: Jun. 5, 2000

Related U.S. Application Data
(60) Provisional application No. 60/137,626, filed on Jun. 4, 1999.

(51) Int. Cl.[7] .................................. A61F 2/44; A61F 2/42
(52) U.S. Cl. .................. 623/23.5; 623/17.15; 623/21.4; 623/17.14
(58) Field of Search .................... 623/17.11, 17.15, 623/21.15, 21.16, 21.11, 23.5

(56) References Cited

U.S. PATENT DOCUMENTS

| | | | |
|---|---|---|---|
| 3,855,638 A | 12/1974 | Pilliar | 3/1 |
| 3,867,728 A | 2/1975 | Stubstad et al. | 3/1 |
| 4,206,516 A | 6/1980 | Pilliar | 3/1.9 |
| 4,309,777 A | 1/1982 | Patil | 3/1.91 |
| 4,349,921 A | 9/1982 | Kuntz | 3/1 |
| 4,501,269 A | 2/1985 | Bagby | 128/92 G |
| 4,714,469 A | 12/1987 | Kenna | 623/17 |
| 4,743,256 A | 5/1988 | Brantigan | 623/17 |
| 4,743,260 A | 5/1988 | Burton | 623/17 |
| 4,759,769 A | 7/1988 | Hedman et al. | 623/17 |
| 4,820,305 A | 4/1989 | Harms et al. | 623/16 |
| 4,834,757 A | 5/1989 | Brantigan | 623/17 |
| 4,863,476 A | 9/1989 | Shepperd | 623/17 |
| 4,863,477 A | 9/1989 | Monson | 623/17 |
| 4,874,389 A | 10/1989 | Downey | 623/17 |

(List continued on next page.)

FOREIGN PATENT DOCUMENTS

| | | | |
|---|---|---|---|
| EP | 0 042 271 A1 | 12/1981 | A61F/1/00 |
| EP | 0 282 161 B1 | 9/1988 | A61F/2/44 |
| EP | 0 284 210 B1 | 9/1988 | A61F/2/44 |
| EP | 0 298 233 A1 | 1/1989 | A61F/2/44 |
| EP | 0 298 235 B1 | 1/1989 | A61F/2/08 |
| EP | 0 302 719 A1 | 2/1989 | A61F/2/44 |
| EP | 0 346 129 A1 | 12/1989 | A61F/2/44 |
| EP | 0 356 112 A1 | 2/1990 | A61F/2/44 |
| EP | 0 392 076 A1 | 10/1990 | A61F/2/44 |
| EP | 0 465 514 B1 | 1/1992 | A61F/2/44 |
| EP | 0 471 821 B1 | 2/1992 | A61F/2/44 |
| EP | 0 505 634 B1 | 9/1992 | A61L/27/00 |
| EP | 0 517 030 A2 | 12/1992 | A61F/2/44 |
| EP | 0 563 332 B1 | 10/1993 | A61F/2/44 |
| EP | 0 642 775 A1 | 3/1995 | A61F/2/44 |

(List continued on next page.)

*Primary Examiner*—David H. Willse
*Assistant Examiner*—Suzette J. Jackson
(74) *Attorney, Agent, or Firm*—Wolf, Greenfield & Sacks, P.C.

(57) ABSTRACT

Disclosed is an orthopedic implant suitable for arthroplasty procedures. The orthopedic implant includes a first plate, a second plate, an axial support between the first plate and the second plate and one or more torsional supports connecting the first plate and the second plate. The axial support may be, for example, one or more flexible struts, such as cables, or a ball and socket joint. The torsional supports connect the first and second plates and may be, for example, curved around the axial support. The torsional supports may be integrally formed with the first and second plates as a single unitary device, by, for example, a Laser Engineered Net Shape (LENS) process.

28 Claims, 1 Drawing Sheet

U.S. PATENT DOCUMENTS

| | | | |
|---|---|---|---|
| 4,878,915 A | 11/1989 | Brantigan | 623/17 |
| 4,904,261 A | 2/1990 | Dove et al. | 623/17 |
| 4,911,718 A | 3/1990 | Lee et al. | 623/17 |
| 4,917,704 A | 4/1990 | Frey et al. | 623/17 |
| 4,932,975 A * | 6/1990 | Main et al. | 623/17.11 |
| 4,936,848 A | 6/1990 | Bagby | 623/17 |
| 4,946,378 A | 8/1990 | Hirayama et al. | 623/17 |
| 4,955,908 A | 9/1990 | Frey et al. | 623/17 |
| 4,961,740 A | 10/1990 | Ray et al. | 606/61 |
| 5,002,576 A * | 3/1991 | Fuhrmann et al. | 623/17.11 |
| 5,015,247 A | 5/1991 | Michelson | 606/61 |
| 5,026,373 A | 6/1991 | Ray et al. | 606/61 |
| 5,035,716 A | 7/1991 | Downey | 623/17 |
| 5,059,193 A | 10/1991 | Kuslich | 606/61 |
| 5,071,437 A | 12/1991 | Steffee | 623/17 |
| 5,123,926 A | 6/1992 | Pisharodi | 623/17 |
| 5,171,281 A | 12/1992 | Parsons et al. | 623/17 |
| 5,192,327 A | 3/1993 | Brantigan | 623/17 |
| 5,246,458 A | 9/1993 | Graham | 623/17 |
| 5,258,031 A | 11/1993 | Salib et al. | 623/17 |
| 5,282,863 A | 2/1994 | Burton | 623/17 |
| 5,314,477 A | 5/1994 | Marnay | 623/17 |
| 5,314,478 A | 5/1994 | Oka et al. | 623/18 |
| 5,320,644 A | 6/1994 | Baumgartner | 623/17 |
| 5,390,683 A | 2/1995 | Pisharodi | 128/898 |
| 5,401,269 A | 3/1995 | Büttner-Janz et al. | 623/17 |
| 5,425,772 A | 6/1995 | Brantigan | 623/17 |
| 5,425,773 A | 6/1995 | Boyd et al. | 623/17 |
| 5,443,515 A | 8/1995 | Cohen et al. | 623/17 |
| 5,458,638 A | 10/1995 | Kuslich et al. | 623/17 |
| 5,458,643 A | 10/1995 | Oka et al. | 623/18 |
| 5,484,437 A | 1/1996 | Michelson | 606/61 |
| 5,489,308 A | 2/1996 | Kuslich et al. | 623/17 |
| 5,505,732 A | 4/1996 | Michelson | 606/61 |
| 5,514,180 A | 5/1996 | Heggeness et al. | 623/17 |
| 5,522,898 A | 6/1996 | Bao | 623/17 |
| 5,522,899 A | 6/1996 | Michelson | 623/17 |
| 5,529,736 A * | 6/1996 | Shalaby et al. | 264/162 |
| 5,534,030 A | 7/1996 | Navarro et al. | 623/17 |
| 5,545,229 A | 8/1996 | Parsons et al. | 623/17 |
| 5,549,607 A | 8/1996 | Olson et al. | 606/61 |
| 5,549,700 A * | 8/1996 | Graham et al. | 623/22.15 |
| 5,554,191 A | 9/1996 | Lahille et al. | 623/17 |
| 5,562,738 A | 10/1996 | Boyd et al. | 623/17 |
| 5,571,190 A | 11/1996 | Ulrich et al. | 623/17 |
| 5,593,409 A | 1/1997 | Michelson | 606/61 |
| 5,607,424 A | 3/1997 | Tropiano | 606/61 |
| 5,609,637 A | 3/1997 | Biedermann et al. | 623/17 |
| 5,645,597 A | 7/1997 | Krapiva | 623/17 |
| 5,674,294 A | 10/1997 | Bainville et al. | 623/17 |
| 5,674,296 A | 10/1997 | Bryan et al. | 623/17 |
| 5,683,465 A | 11/1997 | Shinn et al. | 623/17 |
| 5,702,449 A | 12/1997 | McKay | 623/17 |
| 5,702,450 A | 12/1997 | Bisserie | 623/17 |
| 5,702,451 A | 12/1997 | Biedermann et al. | 623/17 |
| 5,702,454 A | 12/1997 | Baumgartner | 623/17 |
| 5,705,780 A | 1/1998 | Bao | 204/157.15 |
| 5,716,416 A | 2/1998 | Lin | 623/17 |
| 5,735,899 A | 4/1998 | Schwartz et al. | 623/17 |
| 5,741,253 A | 4/1998 | Michelson | 606/61 |
| 5,755,796 A | 5/1998 | Ibo et al. | 623/17 |
| 5,755,797 A | 5/1998 | Baumgartner | 623/17 |
| 5,772,661 A | 6/1998 | Michelson | 606/61 |
| 5,776,199 A | 7/1998 | Michelson | 623/17 |
| 5,782,919 A | 7/1998 | Zdeblick et al. | 623/17 |
| 5,785,710 A | 7/1998 | Michelson | 606/61 |
| 5,797,909 A | 8/1998 | Michelson | 606/61 |
| 5,800,549 A | 9/1998 | Bao et al. | 623/17 |
| 5,824,094 A | 10/1998 | Serhan et al. | 623/17 |
| 5,827,328 A * | 10/1998 | Butterman | 623/17.15 |
| 5,860,973 A | 1/1999 | Michelson | 606/61 |
| 5,865,848 A | 2/1999 | Baker | 623/17 |
| 5,888,226 A | 3/1999 | Rogozinski | 623/17 |
| 5,893,889 A | 4/1999 | Harrington | 623/17 |
| 5,895,428 A * | 4/1999 | Berry | 623/17.15 |
| 5,919,234 A | 7/1999 | Lemperle et al. | 623/16 |
| 5,919,235 A | 7/1999 | Husson et al. | 623/17 |
| 5,928,284 A | 7/1999 | Mehdizadeh | 623/17 |
| 5,976,186 A | 11/1999 | Bao et al. | 623/17 |
| 6,007,580 A * | 12/1999 | Lehto et al. | 623/21.11 |
| 6,019,759 A | 2/2000 | Rogozinski | 606/61 |
| 6,019,792 A | 2/2000 | Cauthen | 623/17 |
| 6,025,538 A | 2/2000 | Yaccarino, III | 623/16 |
| 6,045,579 A | 4/2000 | Hochshuler et al. | 623/17 |
| 6,045,580 A | 4/2000 | Scarborough et al. | 623/17 |
| 6,063,088 A | 5/2000 | Winslow | 606/61 |
| 6,093,205 A * | 7/2000 | McLeod et al. | 623/17.11 |

FOREIGN PATENT DOCUMENTS

| | | | |
|---|---|---|---|
| EP | 0 706 354 B1 | 4/1996 | A61F/2/44 |
| EP | 0 732 093 A2 | 9/1996 | A61F/2/44 |
| EP | 0 773 008 A1 | 5/1997 | A61F/2/44 |
| EP | 0 832 622 A2 | 4/1998 | A61F/2/44 |
| WO | WO 90/11740 | 10/1990 | A61F/2/44 |
| WO | WO 97/26847 | 7/1997 | A61F/2/44 |
| WO | WO 98/17207 | 4/1998 | A61F/2/44 |
| WO | WO 98/22050 | 5/1998 | A61F/2/44 |
| WO | WO 98/34552 | 8/1998 | A61B/17/70 |
| WO | WO 99/00074 | 1/1999 | A61F/2/44 |
| WO | WO 99/02108 | 1/1999 | A61F/2/44 |
| WO | WO 99/05995 | 2/1999 | A61F/2/44 |
| WO | WO 99/20209 | 4/1999 | A61F/2/44 |
| WO | WO 99/22675 | 5/1999 | A61F/2/44 |
| WO | WO 99/53871 | 10/1999 | A61F/2/44 |
| WO | WO 99/65425 | 12/1999 | A61F/2/44 |

* cited by examiner

ORTHOPEDIC IMPLANT

This application claims priority under 35 U.S.C. §119(e) to U.S. Provisional Application Ser. No. 60/137,626, filed Jun. 4, 1999, titled METHOD, APPARATUS, DESIGN AND MANUFACTURE OF DEVICES FOR TISSUE REPAIR, TRANSPLANTATION AND SURGICAL RECONSTRUCTION.

FIELD OF THE INVENTION

The present invention is directed to an orthopedic implant. More specifically, the orthopedic implant is suitable for arthroplasty procedures where optimized multifunctional behavior of the implant is desired. The implant may include the ability for load sharing between the implant and host bone, and the restoration of motion, such as in the replacement of a spinal disc.

DESCRIPTION OF THE RELATED ART

Orthopedic implants have been used in the past to repair damage to the skeleton and related structures, and to restore mobility and function. For example, various devices, such as pins, rods, surgical mesh and screws, have been used to join fractured bones in the proper orientation for repair.

Implants that restore the function to a damaged joint have also been used. Surgery intended to restore function to a joint is referred to as arthroplasty. A successful arthroplasty may eliminate pain and prevent the degradation of adjacent tissue. Arthroplasty has been performed on knees, hips and shoulders by replacing portions of the joint with implants. Presently available implants for arthroplasty may result in stress shielding, meaning that the stress normally felt by bone adjacent to the implant is reduced due to the stiffness of the implant. When a bone is stress shielded, it typically reduces in size and strength according to Wolf's Law, increasing the chance of breakage.

In some instances, instead of replacing a damaged joint, the joint is merely fused in a single position. Surgery intended to fuse a joint rather than to restore mobility is referred to as arthrodesis. Arthrodesis is particularly common for the complex load-bearing joints of the spine. Spinal fusion may be performed to remedy failure of a spinal disc. Spinal discs perform spacing, articulation, and cushioning functions between the vertebrae on either side of the disc. If the normal properties of a disc are compromised, these functions can be seriously reduced. Disc collapse or narrowing reduces the space between vertebrae, and damage to the disc can cause it to bulge or rupture, possibly extruding into the spinal canal or neural foramen. These changes can cause debilitating back and distal pain, numbness, or weakness.

Orthopedic implants may be used in arthrodesis to stabilize the spine and promote fusion. The two main approaches to implant-aided spinal fusion are anterior and posterior. Anterior fusion techniques are widely used, primarily due to the recent appearance of Interbody Fusion Devices (IBFDs). IBFDs are inserted from an anterior approach into the space normally occupied by the disc for space retention, stabilization and load bearing. Posterior fusion is accomplished by cutting through the musculature of the back, exposing the spinal segments, and fixing adjacent vertebra using hardware typically consisting of metal rods, screws, and other devices. Bone harvested from the patient's iliac crest (autograft), donor bone (allograft), or other synthetic biocompatible material is sometimes also packed into the space to induce fusion.

U.S. Pat. No. 5,860,973 (Michelson) discloses an implant which is placed translaterally between two discs. The implant, which is typically installed as a pair of implants, is cylindrical and is filled with fusion promoting material. During the installation, holes are bored between the vertebra and the implant is placed within the holes. The vertebra then grow toward one another and fuse together.

Another way to treat spinal damage is to replace the damaged vertebra or disc with some form of spacer. For example U.S. Pat. No. 5,702,451 (Biedermann) discloses a space holder for a vertebra or spinal disc consisting of a hollow sleeve perforated with diamond-shaped holes. The holes are sized and arranged such that when different lengths of sleeve are cut, the recesses along the edge of the cut resulting from the diamond shaped holes are uniform and able to be mated with projections on an end cap.

Both spinal fusion, such as disclosed by Michelson, and the use of spacers, such as disclosed by Biedermann, limit the mobility of the spine by fixing two adjacent vertebra relative to one another. In addition to reduced mobility, these arrangements do not compensate for the shock absorption lost when a disc is damaged or removed.

Attempts to restore lost function to damaged spinal joints (arthroplasty) have also been made. For example, replacement of entire discs or simply the nucleus pulposus (center portion of the disc) have been proposed. Some attempts use elastomers to mimic the shock absorption and flexibility of the natural disc. However, the complex load bearing behavior of a disc has not been successfully reproduced with an elastomer, and such implants are prone to wear and failure. For example, U.S. Pat. No. 5,674,294 (Bainville) describes an intervertebral disc spacer having two metal half-envelopes which confine between them a cushion. Similarly, implants using various liquids and gels have also been attempted. These implants are subject to failure by rupture or drying out, just like a disc. Mechanical approaches to disc replacement have also been attempted. For example, articulating surfaces and spring-based structures have been proposed. In addition to failing to accurately perform the functions of the replaced disc, these structures are multi-component and particles due to wear of articulating components can result in adverse biological responses or increase the possibility of mechanical failure. For example, U.S. Pat. No. 5,893,889 (Harrington) describes an artificial disc having upper and lower members joined by a pivot ball and having a shock absorbing members fitted between the upper and lower member.

Total hip arthroplastics that use rigid stems as the load sharing devices between the femur and the acetabulum have been observed to experience the phenomena referred to as stress shielding also. In this case, the method of load transfer has been changed with the insertion of the implant. In the normal femur, the loads are applied to the femoral head and transferred along the length of the femur through the cortical shell of the femur. In the case of the femur with an implant, the loads are applied to the prosthesis which transfers the loads distally down the prosthesis and gradually transfer the loads from the prosthesis to the inside of the cortical shell. This results in a significant portion of the proximal portion of the femur no longer experiencing a normal stress condition. This condition will then result in a loss of bone mass surrounding the distal portion of the device. Consequences of this bone loss include loss of support for the device, which will allow the device to move and become painful, and, should revision of the device required, then there may be insufficient bone for support of the subsequent implant.

A number of approaches have been attempted to solve this problem. These include use of composite materials for controlled stiffness of the bulk material, modifications of the cross section of the device to reduce stiffness (this includes local reduction in cross section and hollow stems) and incorporation of slits in the device to increase flexibility. None of these approaches have been successful in that the compromises required to achieve the reduction in stiffness did not find the proper compromise between the required strengths and stiffness.

In total knee arthroplastics wear surfaces are typically made up of two materials, a polymer and a metal. Typically, ultra high molecular weight polyethylene (UHMWPE) is used as the polymer. While this material has excellent wear properties, it is not a wear free surface. The cartilage of the normal knee is capable of producing a fluid film upon the application of mechanical stresses to it. This fluid film is then used as a lubricant to reduce the coefficient of friction between the two cartilage wear surfaces. There is no fluid film lubricant in the total knee joint implants presently known. Instead the materials articulate directly on one other resulting in the generation of wear debris and possibly adverse biological responses.

Several attempts have been made to incorporate stochastic foam materials to reproduce this fluid film lubrication mechanism in the knee joint. However none of these approaches have been successful in reproducing the functionally graded material properties required for this application.

SUMMARY

Accordingly, one embodiment of the present invention is directed to an orthopedic implant including a first plate, a second plate, an axial support between the first plate and the second plate, and one or more torsional supports connecting the first plate and the second plate. The torsional supports, the first plate and the second plate may be integrally formed.

BRIEF DESCRIPTION OF THE DRAWINGS

Preferred, non-limiting embodiments of the present invention will be described by way of example with reference to the accompanying drawings, in which.

DETAILED DESCRIPTION

Figure 1:
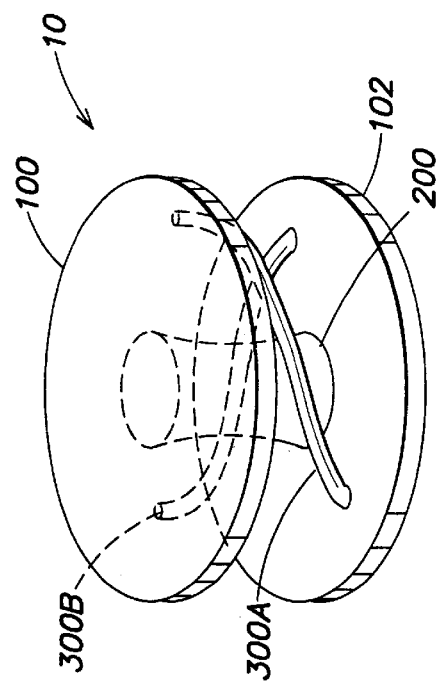
FIG. 1 is a perspective view of one embodiment of an orthopedic implant of the present invention.

The design of an optimized implant for use in arthroplasty, such as spinal disc replacement, may be achieved through several methods. Preferably, such a device is designed using functionally adapted software, such as that described in U.S. patent application Ser. No. 09/400,516, titled "METHOD AND APPARATUS FOR DESIGNING FUNCTIONALLY ADAPTED STRUCTURES HAVING PRESCRIBED PROPERTIES," which is herein incorporated by reference. This design methodology involves the use of a seed geometry that has been screened for a prescribed set of mechanical properties. The seed geometry may be adjusted to fill a design envelope defined as the space available for an implant as determined from anatomical studies. A set of inputs may then be determined representing the functional requirements for a clinically successful implant. The next step may be to optimize the seed geometry using functionally adapted software, such as that described in the above-mentioned U.S. Patent Application. In the case of a lumbar spinal disc replacement, loading conditions and corresponding stiffness requirements may be used as the input conditions for the optimization algorithm. Additional criteria also may be applied, such as maintaining peak stresses at a stress level at or below the fatigue endurance limit of the material the implant is to be fabricated from.

In addition to functionally adapted software mentioned above, there are several other approaches that can be taken to optimize the structure. For example, commercially available software packages such as Pro Engineer produced by Parametric Technologies Corporation of Waltham, Mass. and ANSYS produced by ANSYS, Inc. of Canonsburg, Pa. may be used to optimize some parameters based on, for example, geometric considerations, material properties and the functional properties of the joint to be replaced.

The seed geometries used for the optimization process may be taken from a library of three dimensional geometries such as that available from Molecular Geodesics, Inc. of Boston, Mass. Examples of these geometries are structures such as octet trusses and kelvin foams. These seed geometries may be combined in a continuous or discontinuous manner. The combination of these geometries is known as combinatorial geodesics.

The seed geometries need not be homogeneous. Instead, for example, if anisotropic properties are desired, the seed geometries may be adjusted such that these are also anisotropic. Thus, an implant may include differing seed geometries. These seed geometries may be solid, porous or other standard manufacturing constructs such as braids, woven materials or laminates. Furthermore, the seed geometries are not required to be constant in cross section, instead, the geometric properties of the cross section may be varied throughout the structure.

One key feature to the design of implants using the techniques described above is the recognition that designs do not have to be limited to the traditional manufacturing constraints such as those imposed by conventional machining or casting methods. These methods have limitations regarding the size and shape of the features that may be produced. Construction of implants designed using the techniques described above may be with the use of other manufacturing techniques such as solid free form fabrication. Some examples of solid free form fabrication include, but are not limited to, directed deposition of metals (also known as Laser Engineered Net Shape [LENS] processes), Selective Laser Sintering (SLS) and 3D printing. All of these approaches may be used in combination with the Hot Isostatic Pressing (HIP) process to produce a product substantially free of internal porosity and defects. The LENS process includes directing a stream of metal powder into a mobile laser which melts the metal. As the laser moves, the metal solidifies. Subsequent layers of metal may be deposited on one another, allowing a three dimensional structure to be built up. The LENS process is described more fully in U.S. Pat. No. 6,046,426 (Jeanette) and U.S. Pat. No. 5,993,554 (Keicher) and these patents are hereby incorporated by reference. The combination of these manufacturing techniques and the optimization approaches described above allow for the design, optimization and manufacture of novel structures with multifunctional features according to the invention. In particular, according to the invention, there are provided novel implant structures, such as unitary structures, that have significant variations in stiffness in the axial and flexion/extension orientations.

Referring now to the figures, and in particular to FIG. 1, one example embodiment of an orthopedic implant according to an embodiment of the invention is illustrated. Orthopedic implant 10 includes a first plate 100, a second plate 102, an axial support 200 between plates 100, 102 and one or more torsional supports 300A, 300B connecting the first plate and the second plate. As used herein, the axial means along an axis that is substantially perpendicular to the primary surfaces of plates 100, 102 and an axial support is a structure that provides support and resistance to compression in the axial direction. As used herein, torsion refers to both twisting and bending and torsional support refers to a structure providing resistance and support against twisting or bending.

Figure 4:
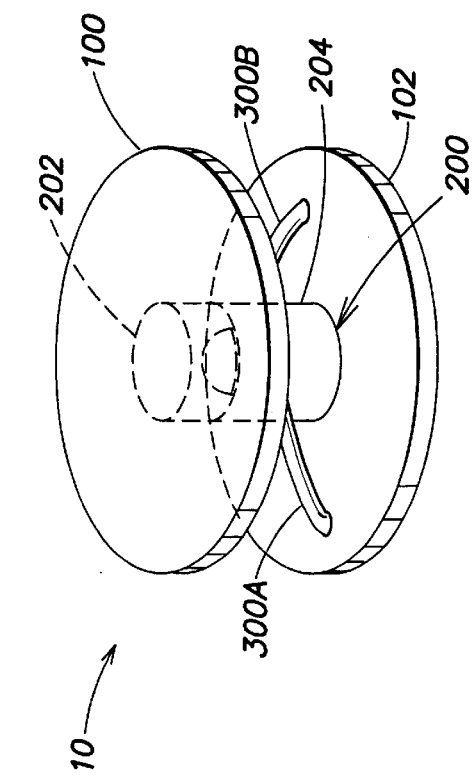
FIG. 4 is a perspective view of another embodiment of an orthopedic implant of the present invention.

First and second plates 100, 102 may be of any material and constructed in any manner that allows plates 100, 102 to establish a stable interface with adjacent tissue and that are safe for an implant recipient. For example, where implant 10 completely replaces a joint between two bones, plates 100, 102 may be constructed to establish a stable interface with adjacent bone. Establishing a stable interface may have both short and long term components. Specific structure may be included on plates 100, 102 to address each component. For example, plates 100, 102 may have structure ensuring that implant 10 remains in a desired location in the short term, following implantation. This structure may include, for example, protrusions 400, as illustrated in FIG. 4, such as, for example, teeth, ridges or serrations. Plates 100, 102 may also be constructed to interact with other fixation devices. For example, plates 100, 102 may have holes 12 for receiving bone screws which may be used to affix them to the bone. Similarly, plates 100, 102 may have structure ensuring that implant 10 remains in a desired location in the long term, and successfully interfaces with adjacent tissue. This structure may include, for example, a tissue ingrowth region 500 (See FIG. 4) that allows adjacent tissue to grow into the implant, forming a stable interface. Tissue ingrowth region 500 may include porous surfaces, osteoinductive surfaces and osteoconductive surfaces. For example, tissue ingrowth region 500 may comprise sintered metal particles or a structure constructed by solid free form fabrication. The tissue ingrowth region 500 may only include enough of plates 100, 102 to establish a stable interface with adjacent tissue and plates 100, 102 may be predominantly solid.

It is to be appreciated that first and second plates 100, 102 may also be sized and shaped to establish a stable interface with adjacent tissue. For example, plates 100, 102 need not be flat and may be shaped to match the contour of adjacent tissue. For example, if the tissue adjacent to one of plates 100, 102 is concave or convex, the plate 100, 102 may be constructed with a curved shape to match the adjacent tissue of the joint. Similarly, plates 100, 102 need not be circular or oval as illustrated in FIGS. 1–4, rather, they may be any shape that allows establishment of a stable interface with adjacent tissue. Accordingly, implant 10 may have an irregular shape corresponding to an adjacent tissue such as a bone. For example, where implant 10 is used to replace an intervertebral disc, it may be shaped like a spinal disc, allowing it to fit easily between the vertebra and to establish a stable interface therewith.

It is to be appreciated that first and second plates 100, 102 may be constructed of any material that is safe for a recipient of implant 10, and that allows a stable interface with adjacent tissue. For example, plates 100, 102 may be constructed of a material that is biocompatible, meaning that it is neither harmful to the health of an implant recipient, nor significantly damaged or degraded by the recipient's normal biology. Biocompatible materials include, for example, various metals and metal alloys, ceramic materials and synthetic materials, such as polymers. It is also to be appreciated that plates 100 may also be constructed of a material that is strong and durable enough to withstand the forces that may be placed upon it once installed in an implant recipient. For example, if implant 10 is used to replace a load bearing joint, the material for plates 100, 102 may be selected such that plates 100, 102 will not fail under stresses normally experienced by that joint, The ability of plates 100, 102 to withstand stresses also may be dependant on the shape and size of plates 100, 102 as well as their material of construction and, thus, it is to appreciate that the size and shape of plates 100, 102 may also be considered when selecting a material. In one embodiment of an implant according to the invention, plates 100, 102 are preferably constructed of titanium or a titanium alloy. A titanium alloy typically used in implants includes 6% aluminum and 4% vanadium by weight.

Figure 2:
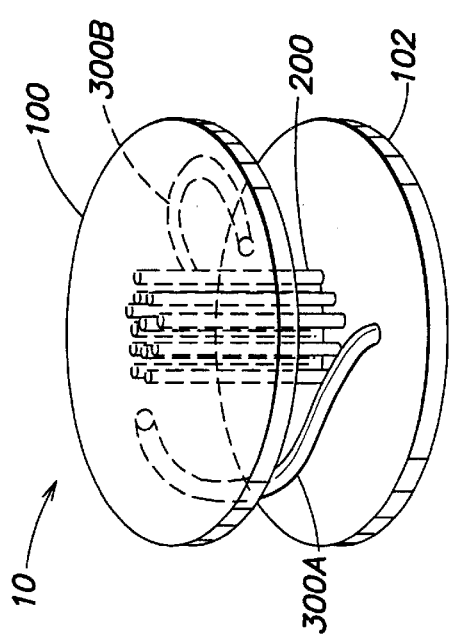
FIG. 2 is a perspective view of another embodiment of an orthopedic implant of the present invention.
Figure 3:
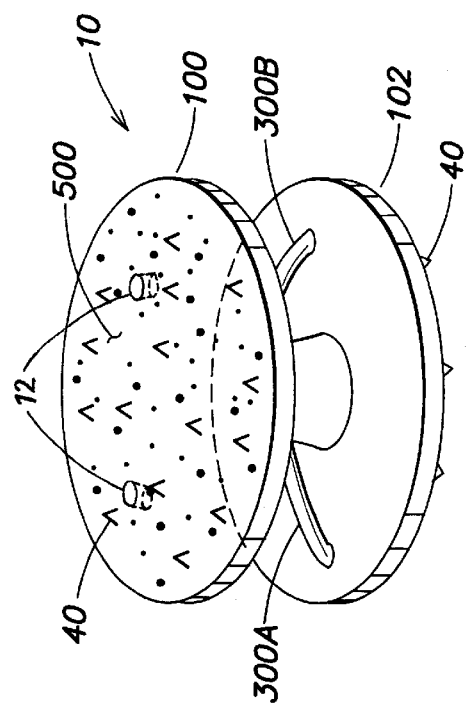
FIG. 3 is a perspective view of another embodiment of an orthopedic implant of the present invention.

Referring now to FIGS. 1–3, it is to be appreciated that axial support 200 may by constructed of any materials and in any manner that provides sufficient support and flexibility for a successful arthroplasty and is safe for the implant recipient. Axial support 200 may be constructed in a manner so that it provides support along an axis that is substantially perpendicular to the primary surfaces of plates 100, 102. This support may be sufficient for implant 10 to successfully bear loads that may be placed upon it, However, axial support 200 may also be constructed in a manner so that it provides flexibility so that it may successfully restore motion to a joint it replaces. For example, axial support 200 may be constructed as one or more struts or of first and second mating halves 202, 204 that provide sufficient support and flexibility to implant 10.

Where axial support 200 is constructed as one or more struts, the struts may be constructed to provide axial support to implant 10 and also to be flexible. For example, the struts may be relatively incompressible and may be arranged substantially perpendicular to plates 100, 102 as illustrated in FIG. 1. Accordingly, stress applied parallel to, and directly above, the struts will be resisted by each strut due to its incompressibility. Conversely, stresses not parallel to, or directly above, the struts will result in bending of the struts due to their flexibility.

In one embodiment of the implant of the invention, the struts may be cables. Cables are typically relatively incompressible along their lengths and are also typically flexible. Accordingly, an axial support 200 constructed of one or more cables would provide support sufficient to replace the load bearing function of a joint while also allowing it to flex, resulting in a successful arthroplasty implant.

Axial support 200 may also comprise a single strut shaped to be flexible. For example, axial support 200 may comprise a strut that is tapered in a center region, as illustrated in FIGS. 2 and 4. Although the strut is illustrated in FIGS. 2 and 4 as having an oval cross-section, any shape providing the desired support and flexibility for axial support 200 may be used.

Where axial support 200 is constructed of mating halves 202, 204, it may be constructed to provide sufficient support and flexibility for a successful arthroplasty and to provide a stable connection between halves 202, 204. Halves 202, 204 constructed to provide a stable connection may be constructed such that they may not slip off of one another or otherwise become detached from one another. Halves 202, 204 may also be constructed such that axial support 200 is still flexible. For example, halves 202, 204 may form a joint capable of articulation, such as, for example, a ball and socket joint that may be sufficiently stable to withstand stresses typically applied to a joint, yet that will not detach, and that is articulable to provide flexibility to axial support 200.

It is to be appreciated that axial support 200 may be located anywhere between plates 100, 102 to provide support and flexibility at any portion of plates 100, 102. The location of axial support 200 may depend on the nature of implant 10 and the type of joint being replaced. Typically, axial support 200 will be located at the point about which the joint it replaces normally pivots. This may be near the center of plates 100, 102, however, it need not be. Axial support 200 may be connected to the plates 100, 102 by any method that will maintain it in a proper location and is not subject to failure. For example, axial support 200 may be welded to plates 100, 102, or it may be integrally formed with plates 100, 102 such as described above using the LENS process.

It is to be appreciated that axial support 200 may be constructed of any material that is safe for a recipient of implant 10 and can withstand the stresses and friction that will be placed upon it. For example, axial support 200 may be constructed of a material that is biocompatible. Axial support 200 may also be constructed of a material that is strong and durable enough to withstand the forces that may be placed upon it once installed in an implant recipient. For example, if implant 10 is used to replace a load bearing joint, the material axial support 200 is constructed from may be selected such that axial support 200 does not fail under stresses normally experienced by that joint. The ability of axial support 200 to withstand stresses also may be dependant on the shape and size of axial support 200 as well as its material of construction and, thus, size and shape of axial support 200 may also be considered when selecting a material. Where axial support 200 also comprises an articulating joint, the material that axial support 200 is constructed from may be selected to be resistant to frictional wear. In one embodiment of an implant according to the invention, axial support 200 is preferably constructed of titanium or a titanium alloy.

Where axial support 200 is a single piece of material it may be fabricated from a polymer or composite of a polymer and other reinforcement. Typical reinforcements include but are not limited to carbon or glass fibers, either continuous or chopped in form. Other reinforcements may be thin sheets of metals that are laminated together using polymers as adhesives. The size, shape, orientation and amount of these reinforcements may be such that the mechanical properties of axial support 200 can be engineered to meet the flexibility and strength requirements.

It is also to be appreciated that torsional supports 300A, 300B may be constructed of any material and in any manner that provides sufficient resistance to bending and torsion of implant 10 to allow implant 10 to provide the torsional support function of the joint replaced, but that is sufficiently flexible to allow implant 10 to bend or turn where desired, such as in twisting or bending of a spinal implant according to the normal movement of the spinal column. Torsional supports may also be constructed of a material and in a manner that is safe for a recipient of implant 10. Torsional supports 300A, 300B also may be constructed in a manner that provides sufficient resistance to bending and torsion to allow implant 10 to support surrounding tissue and prevent injury due to excessive bending or torsion, For example, axial support 200 may be flexible and may not provide sufficient resistance to bending or torsion. Accordingly, if torsional supports 300A, 300B do not provide sufficient resistance to bending and rotation, implant 10 may allow over-rotation or excessive bending of a joint, potentially resulting in injury. For example, where implant 10 is used to replace a spinal disc, over rotation or excessive bending could result in pain or damage to the nerves of the spinal column. Accordingly, torsional supports 300A, 300B preferably provide some resistance to bending and may also allow torsional supports 300A, 300B to perform some of the shock absorbing function that the replaced joint had.

While torsional support 300A, 300B may provide some resistance to torsion or bending, torsional supports 30A, 300B are preferably provided so that this resistance should is not so great that desired motion of the joint is lost. For example, it may be desired to restore a full range of motion to a joint replaced by implant 10, and torsional support 300A, 300B may have a degree of resistance to torsion and bending that limits the implant to the range of motion of the original joint, but not more than this.

In one embodiment of an implant of the invention, torsional support 300A, 300B may be comprised of one or more struts to provide resistance to torsion and bending while still allowing desired motion. For example, one or more struts may extend from first plate 100 to second plate 102. The struts may be arranged such that, unlike axial support 200, pressure directly against plates 100, 102 at the ends of the struts will not be resisted by the struts due to their incompressibility, but rather, the struts act as a spring. For example, the struts may be curved, or the top and bottom of these struts may not be directly above one another. As illustrated in FIGS. 1–4, struts may curve around some portion of axial support 200 while extending between plates 100, 102, providing simultaneous flexibility and resistance both to torsion and to bending of implant 10 around axial support 200.

It is to be appreciated where even resistance to bending and torsion is desired for implant 10, torsional supports 300A, 300B may be symmetrical. For example, where there are two torsional supports 300A, 300B, the torsional supports may be mirror images of one another as illustrated in FIG. 2, or where there are more than two torsional supports 300A, 300B, they may be equally spaced around axial support 200. Where even resistance to bending and torsion is not desired, torsional supports 300A, 300B may be asymmetrical to provide more resistance where more resistance is desired, or more torsional supports may be used at these locations.

It is to be appreciated that torsional supports 300A, 300B may be constructed by any method that will provide desired properties and long life. For example, torsional supports may be cast, machined or otherwise formed and then attached to plates 100, 102, such as by welding. However, one possible disadvantage of manufacturing torsional supports 300A, 300B separately from plates 100, 102, in other words other than as a unitary structure, is that the points of attachment may weaken and be subject to fatigue and possibly failure. Furthermore, if the struts are bent or twisted once formed, this deformation may result in micro-cracking and other structural degradation. Accordingly, in one embodiment of an implant according to the invention, it is preferred that torsional supports 300A, 300B are integrally formed with plates 100, 102, For example, plates 100, 102 and torsional support 300A, 300B may be formed by the LENS process. For example, implant 10 formed by the LENS process may be comprised of solid metal and may be formed in the exact shape desired, eliminating the need to attach torsional support 300A, 300B to plates 100, 102 or to twist or bend torsional support 300A, 300B.

It is to be appreciated that torsional supports 300A, 300B may be constructed of any material that is safe for a recipient of implant 10, that can withstand the stresses that will be placed upon it, and that also has sufficient flexibility to allow desired motion of implant 10. For example, torsional supports 300A, 300B may be constructed of a material that is biocompatible. Torsional support 300A, 300B may also be constructed of a material that is strong and durable enough to withstand the forces that may be placed upon it once installed in an implant recipient. For example, torsional supports 300A, 300B may be constructed from a material such that torsional supports 300A, 300B may not fail under stress or repeated bending normally experienced by a joint it replaces. The ability of torsional supports 300A, 300B to withstand stresses also may be dependant on the shape and size of torsional supports 300A, 300B as well as their material of construction and, thus, size and shape of torsional supports 300A, 300B may also be considered when selecting a material. In one embodiment of an implant of the invention, torsional supports 300A, 300B are preferably formed of a metal, and this metal is the same as that used to form plates 100, 102 to facilitate construction by the LENS technique. Accordingly, it is also preferred that torsional supports 300A, 300B are constructed of titanium or a titanium alloy.

The implant of the present invention will be further illustrated by the following example which is intended to be illustrative in nature and not considered as limiting to the scope of the invention.

EXAMPLE

One suitable construction of an implant having a shape and design substantially in accordance with the present invention is provided by the following combination of elements.

An implant 10 to be used in a spinal arthroplasty includes a first plate 100 and a second plate 102. Plates 100, 102 are substantially oval and planar and are sized to fit within a human spinal column in a space previously occupied by a disc. The outer planar surfaces of plates 100, 102 are provided with protrusions 400 consisting of teeth and a tissue ingrowth region 500 consisting of a textured surface.

Implant 10 also includes an axial support 200, between, and connecting, plates 100, 102. Axial support 200 is oriented in the center of plates 100, 102 and includes a cable incorporated at both ends to plates 100, 102. Implant 10 further includes two torsional supports 300A, 300B. Torsional supports 300A, 300B are integrally formed with plates 100, 102 and curve around axial support 200 such that the first end of each of torsional supports 300A, 300B is not directly across from the second end of each of torsional supports 300A, 300B. Torsional supports 300A, 300B are mirror images of one another. Implant 10 is constructed of an alloy of titanium with 6% aluminum and 4% vanadium by weight.

Implant 10 may has an outer envelope of approximately 20 mm in the anterior/posterior direction, 30 mm in the lateral direction, and 12 to 15 mm in height. The overall shape mimics that of a vertebral body and is roughly kidney shaped. The size of torsional supports 300A, 300B are dependant on the material selected, but will be about 5 mm or less in diameter. Axial support 200 will be about 10 mm in diameter.

Having thus described at least one preferred embodiment of the implant and method of the invention, various alterations, modifications and improvements will readily occur to those skilled in the art. Such alterations, modifications and improvements are intended to be part of the disclosure and to be within the spirit and scope of the invention. Accordingly, the foregoing description is by way of example only and is limited only as defined in the following claims and equivalents thereto.

What is claimed is:

1. An orthopedic implant, comprising:
    a first plate;
    a second plate;
    an axial support between the first plate and the second plate and including one or more flexible struts; and
    one or more torsional supports connected to the first plate and the second plate.

2. The orthopedic implant of claim 1, wherein the torsional supports each comprise a strut connected at a first end to the first plate and at a second end to the second plate.

3. The orthopedic implant of claim 2, wherein the first plate, the second plate and the one or more torsional supports each comprise a single, solid piece.

4. The orthopedic implant of claim 3, wherein the struts are curved around the axial support.

5. The orthopedic implant of claim 4, wherein there are two struts and the struts are mirror images of one another.

6. The orthopedic implant of claim 3, wherein the torsional supports and the first and second plates are constructed of the same material.

7. The orthopedic implant if claim 6, wherein the material is biocompatible.

8. The orthopedic implant if claim 7, wherein the material comprises titanium.

9. The orthopedic implant of claim 1, wherein the torsional supports, the first plate and the second plate are integrally formed.

10. The orthopedic implant of claim 9, wherein the struts are curved around the axial support.

11. The orthopedic implant of claim 10, wherein there are two struts and the struts are mirror images of one another.

12. The orthopedic implant of claim 9, wherein the torsional supports and the first and second plates are constructed of the same material.

13. The orthopedic implant if claim 12, wherein the material is biocompatible.

14. The orthopedic implant of claim 13, wherein the material comprises titanium.

15. The orthopedic implant of claim 1, wherein in a first position the flexible struts are substantially perpendicular to the first plate and the second plate and the first plate and the second plate are substantially parallel to one another.

16. The orthopedic implant of claim 15, wherein the flexible struts are cables.

17. The orthopedic implant of claim 16, wherein the flexible struts are secured at a first end to the first plate and at a second end to the second plate.

18. The orthopedic implant of claim 17, wherein the struts are secured by welds to the first plate and the second plate.

19. The orthopedic implant of claim 1, wherein the axial support comprises a first half connected to the first plate and a second half connected to the second plate.

20. The orthopedic implant of claim 19, wherein the first half mates with the second half.

21. The orthopedic implant of claim 20, wherein the first half is integrally formed with the first plate and the second half is integrally formed with the second plate.

22. The orthopedic implant of claim 1, wherein the first plate and second plate are substantially planar.

23. The orthopedic implant of claim 1, wherein the first plate and the second plate comprise one or more protrusions for attachment to one or more bones.

24. The orthopedic implant of claim 1, wherein the first plate and the second plate comprise openings for inserting a fixation device.

25. The orthopedic implant of claim 1, wherein the first plate and the second plate each comprise a tissue ingrowth region.

26. The orthopedic implant of claim 25, wherein the tissue ingrowth region is porous.

27. The orthopedic implant of claim 26, wherein the tissue ingrowth region comprises sintered metal particles.

28. An orthopedic implant, comprising:

a first plate;

a second plate;

an axial support between the first plate and the second plate, having a first half connected to the first plate that includes a ball and a second half connected to the second plate that includes a socket, the ball and socket sized and arranged such that the first half and second half mate; and one or more torsional supports connected to the first plate and the second plate.

* * * * *